United States Patent [19]

Dutra

[11] 4,120,689

[45] Oct. 17, 1978

[54] BENZYL AND ARYL ESTERS OF N-PHOSPHONOMETHYL GLYCINES, HERBICIDAL COMPOSITIONS AND USE THEREOF

[75] Inventor: Gerard A. Dutra, Ladue, Mo.

[73] Assignee: Monsanto Company, St. Louis, Mo.

[21] Appl. No.: 839,244

[22] Filed: Oct. 4, 1977

Related U.S. Application Data

[63] Continuation-in-part of Ser. No. 644,406, Dec. 29, 1975, abandoned.

[51] Int. Cl.$^2$ .............................. A01N 9/36; C07F 9/09
[52] U.S. Cl. ........................................... 71/86; 71/87; 260/944
[58] Field of Search ....................... 260/944; 71/86, 87

[56] References Cited

U.S. PATENT DOCUMENTS

| | | | |
|---|---|---|---|
| 3,799,758 | 3/1974 | Franz | 71/86 |
| 3,859,183 | 1/1975 | Wagenknecht | 260/941 X |

*Primary Examiner*—Anton H. Sutto
*Attorney, Agent, or Firm*—Arnold H. Cole; Donald W. Peterson

[57] ABSTRACT

Alkyl-[di(benzyl) or di(aryl)]esters of N-phosphonomethyl glycine are produced by the reaction of a dibenzyl or diaryl phosphite with an N-methylene alkyl glycinate trimer. These esters and the hydrolysis products thereof containing at least one benzyloxy or aryloxy group bonded to phosphorus are novel compounds having the formula

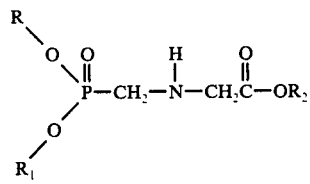

wherein R is a member of the group consisting of phenyl, benzyl, naphthyl, biphenylyl, benzyloxyphenyl and phenyl, benzyl or naphthyl groups substituted with from 1 to 3 groups selected from the class consisting of hydroxyl, lower alkyl, lower alkoxy, lower alkylthio, trifluoromethyl, carbo (lower alkoxy), nitro, or halo; $R_1$ is hydrogen or an R group, and $R_2$ is a lower alkyl group or hydrogen, and the strong acid salts of the compounds wherein neither $R_1$ or $R_2$ is H. These compounds are useful as post-emergent herbicides.

39 Claims, No Drawings

BENZYL AND ARYL ESTERS OF N-PHOSPHONOMETHYL GLYCINES, HERBICIDAL COMPOSITIONS AND USE THEREOF

This is a continuation-in-part of application Ser. No. 644,406, filed Dec. 29, 1975, now abandoned.

This invention relates to derivatives of N-phosphonomethyl glycine containing at least one phosphorus bonded benzyloxy, phenoxy or naphthyloxy group, to herbicidal compositions containing same and to herbicidal methods employing such derivatives. This invention also contemplates a process for producing mixed triesters of N-phosphonomethyl glycine containing a lower alkoxy group bonded to the carbonyl group and two benzyloxy or aryloxy groups bonded to phosphorus.

Trialkyl esters of N-phosphonomethyl glycine are known as well as methods for producing such esters. For example, tetraalkyl esters of N-phosphonomethyl imino diacetic acid can be electrolytically converted to trialkyl esters of N-phosphonomethyl glycine. Most of the trialkyl esters of N-phosphonomethyl glycine are generally ineffective as postemergent herbicides. Esters of N-phosphonomethyl glycine containing an alkyl group attached to the carboxyl group and aromatic or benzyl groups attached to the phosphorus have not yet been specifically described in the literature.

It has now been found that triesters of N-phosphonomethyl glycine wherein an alkyl group is attached to the carboxyl group and aryl or benzyl groups attached to phosphorus are produced by the reaction of a diaryl or dibenzyl phosphite with an alkyl N-methylene glycinate trimer as shown by the following equation which shows for convenience the reaction of diphenyl phosphite with ethyl N-methylene glycinate trimer:

$$3(C_6H_5O)_2\overset{O}{\overset{\|}{P}}-H + (CH_2=N-CH_2-\overset{O}{\overset{\|}{C}}-OC_2H_5)_3 \xrightarrow[heat]{solvent}$$

$$(C_6H_5O)_2\overset{O}{\overset{\|}{P}}-CH_2\overset{H}{\overset{|}{N}}-CH_2-\overset{O}{\overset{\|}{C}}-OC_2H_5.$$

The triester of N-phosphonomethyl glycine can then be treated with strong acid to form salts or can be treated with water to form a hydrolysis product containing a hydroxyl group bonded to phosphorus, the other groups remaining the same. This hydrolysis product can then be further treated with water to produce derivatives of N-phosphonomethyl glycine having a single aryl or benzyl ester group bonded to phosphorus.

Thus, the compounds disclosed herein include those having the formula

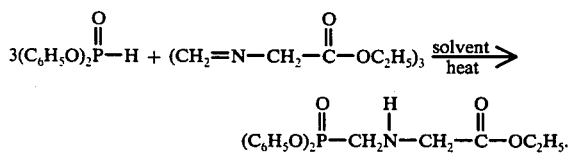

wherein R is a member of the group consisting of phenyl, benzyl, naphthyl, biphenylyl, benzyloxyphenyl and phenyl, benzyl or naphthyl groups substituted with from 1 to 3 groups selected from the class consisting of hydroxyl, lower alkyl, lower alkoxy, lower alkylthio, trifluoromethyl, carbo (lower alkoxy), nitro or halo, $R_1$ is hydrogen or an R group, and $R_2$ is a lower alkyl group or hydrogen, as well as the strong acid salts of those compounds wherein $R_1$ and $R_2$ are other than H groups, i.e. $R_1$ is an R group and $R_2$ is a lower alkyl group.

The compounds of formula I wherein $R_1$ equals R and $R_2$ is an ester group can be treated with a strong acid to form strong acid salts of the formula

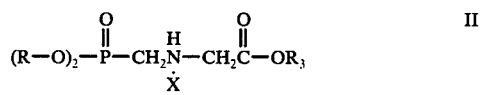

wherein $R_3$ is a lower alkyl group and X is a strong acid.

The triesters of formula I can also be hydrolyzed by mild hydrolysis to yield compounds of the formula

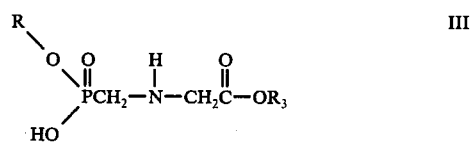

wherein R and $R_3$ are as above defined.

The compounds of formula III can be further hydrolyzed by heating with water and acetone to yield N-phosphonomethyl glycine esters of the formula

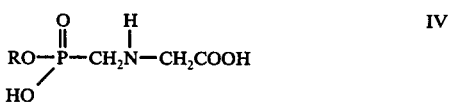

wherein R is as above defined. The term halo or halogen as employed herein means chlorine, bromine, iodine and fluorine.

The term lower alkyl as employed herein means a $C_1$ to $C_4$ alkyl group such as methyl, ethyl, propyl, isopropyl, primary, secondary and tertiary butyl.

Illustrative of the substituted phenyl, benzyl, and naphthyl groups which R and $R_1$ represent are for example, mono and di-halophenyl such as chlorophenyl, dichlorophenyl, chlorobromophenyl, bromophenyl, diiodophenyl, fluorophenyl, chloronaphthyl, chlorobenzyl, dichlorobenzyl, 2, 3 or 4-methylbenzyl, 2, 3 or 4-chlorobenzyl, 2, 3 or 4-nitrobenzyl, hydroxyphenyl, lower alkoxy substituted such as methoxy, ethoxy, propoxy or butoxy-phenyl, benzyl or naphthyl, 2, 3 and 4-carbethoxy-phenyl or benzyl, 2, 3 and 4-nitrophenyl, trifluoromethylphenyl, trifluoromethylbenzyl, 2-chloro-4-methyl phenyl, 2-methyl-4-chlorophenyl and the like.

In accordance with this invention, the triesters of N-phosphonomethyl glycine are produced by the following general procedure:

A solution of phosphite diester of the formula

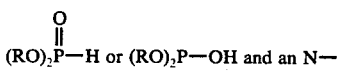

methylene lower alkyl glycinate of the formula

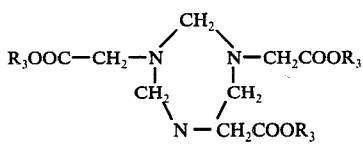

or (CH$_2$=N — CH$_2$COOR$_3$)$_3$ wherein R and R$_3$ are as above defined, is formed in an aprotic solvent which does not react with any of the reagents, and the solution heated to a temperature sufficiently elevated to initiate the reaction between said phosphite and said trimer and then maintained at a temperature sufficient to maintain the reaction for a time sufficient to run the reaction essentially to completion so as to produce a triester of N-phosphonomethyl glycine having the formula

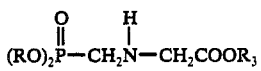

V wherein R and R$_3$ have the above-defined meanings. The triesters of formula V can be isolated by removal of the solvent or they can be employed as a solvent solution.

In conducting the process of this invention, ratios of the phosphite ester to the N-methylene alkyl glycinate trimer of from .1 to 1 to 10 to 1 can be employed. It is of course apparent from the above equation that for best yields and ease of recovery of product, it is preferred to employ ratios of the phosphite ester to trimer of at least 3 to 1.

The solvents which can be employed in producing the triesters of this invention are the anhydrous aprotic solvents which do not react with either the trimer or the phosphite. It is necessary that the solvents be anhydrous so as to prevent premature hydrolysis of the triesters. Examples of such aprotic solvents are acetonitrile, benzene, toluene, xylene, mono and dichlorobenzene, methylene chloride, chloroform, carbon tetrachloride, ethyl acetate, dimethylformamide, tetra hydrofurane, diethyl ether, ethylene glycol dimethylether, diethylene glycol dimethylether and the like. Dimethyl sulfoxide, although aprotic, is not a suitable solvent since it reacts with the phosphite esters.

The temperature at which the process of this invention is conducted is not critical. The temperature should be one which is sufficiently elevated so as to initiate and maintain the reaction. Temperatures in the range of from 20° C. to about 200° C. can be employed. The reaction temperature is generally controlled by the boiling point of the particular solvent employed. Generally it is preferred to employ temperatures in the range of from 80° C. to 170° C. Generally the temperature employed is the reflux temperature of the solvent employed.

The process of this invention can be conducted at atmospheric pressure, subatmospheric pressure or superatmospheric pressure. For convenience and economy, it is preferred to conduct the process of this invention at atmospheric pressure.

The strong acid salts of compounds of formula V are produced by dissolving the compound in a suitable solvent such as acetone or chloroform and a strong acid added. The salt precipitates or diethyl ether is added and the salt forms a solid or insoluble oil.

The strong acids which can be employed to produce the strong acid salts of the compounds of formula I wherein R$_1$ and R$_2$ are other than H, are those which have a pK$_a$ of 2.2 or less as measured in aqueous solution. Acid having a pK$_a$ of as low as 0.1 or even lower can be employed. Examples of such acids are hydrochloric, hydrobromic, hydroiodic, sulfuric acid, chlorosulfonic, methane sulfonic, benzene sulfonic, trichloroacetic, trifluoroacetic, pentafluoropropionic, heptafluorobutyric, trifluoromethane sulfonic acid, oxalic acid and the like.

The mono hydroxy compounds of formula III are produced by mild hydrolysis according to one of the following general methods.

A. A stirred solution of the phosphite ester and the N-methylene lower alkyl glycinate is refluxed in a suitable solvent for from 1 to 2 hours and cooled to room temperature and allowed to stand for a period of time, generally 18 to 60 hours, open to the atmosphere to give a suspension of a solid hydroxy ester of formula III. The solid was washed with acetone and dried to yield an analytically pure sample.

B. A triester of formula I is dissolved in acetone containing 5% by volume water and heated to reflux for approximately 24 hours. After cooling to ambient temperature, the solid hydroxy ester of formula III which formed was removed by filtration and washed once or twice with acetone to yield an analytically pure sample.

The monohydroxy ester produced is converted to a mono ester of formula IV by refluxing it for a period of time sufficient to hydrolyze the carboxylic ester group in an acetone-water mixture. The mono ester of formula IV is recovered as a solid by filtration.

The compounds of this invention are useful as postemergent herbicides.

The following examples serve to further illustrate the invention. All parts are parts by weight unless otherwise expressly stated.

EXAMPLE 1

Di-4-methoxyphenylphosphite (11.72 g, 0.04 mol) and N-methylene ethyl glycinate trimer (4.60 g, 0.0133 mol) were dissolved in 50 ml. of benzene and heated to reflux for 3¼ hours. The benzene was removed under vacuum and the residue filtered through diatomaceous earth to yield 12 grams of ethyl N-[di(4-methoxyphenoxy)phosphonomethyl]glycinate as a light yellow oil which gave the following analysis:

Calc'd: C: 55.75% H: 5.91% N: 3.42%. Found: C: 55.50% H: 6.00% N: 3.45%.

EXAMPLE 2

Di-4-nitrobenzyl phosphite (17.6 g; 0.05 mol) was dissolved in 800 cc. of benzene at about 55° C. N-methylene ethyl glycinate trimer (5.75g, 0.0167 moles) dissolved in benzene (50 ml.) was added and the mixture heated to reflux for 16 hours. The benzene was removed by vacuum evaporation at 50° C. to yield ethyl N-(di-4-nitrobenzyloxyphosphonomethyl)glycinate as a yellow oil which had the following analysis:

Calc'd. C: 48.72%; H: 4.95%; N: 8.97%. Found: C: 48.95%; H: 4.83%; N: 8.70%.

EXAMPLE 3

Diphenylphosphite (11.71g, 0.050 mole) and N-methylene ethyl glycinate trimer (0.0167 mole) were dissolved in benzene (200–300 ml) and heated to reflux for 1–3 hours. The reaction mixture was then vacuum evaporated to remove the benzene to yield ethyl N-(diphenoxyphosphonomethyl)glycinate in a 70% yield which gave the following analysis:

Calc'd. C, 58.45; H, 5.77; N, 4.01. Found: C, 58.47; H, 5.80; N, 4.01.

EXAMPLE 4

Di-4-chlorobenzyl phosphite was reacted with N-methylene ethyl glycinate trimer employing benzene as the solvent in accordance with the above procedure to yield ethyl N-(di-4-chlorobenzyloxyphosphonomethyl)glycinate as a yellow liquid which gave the following analysis:

Calc'd. C, 51.14; H, 4.97; N, 3.14. Found: C, 50.99; H, 4.80; N, 3.19.

EXAMPLE 5

Di-2-methylphenyl phosphite was reacted with N-methylene ethyl glycinate trimer employing benzene as the solvent in accordance with the above procedure to yield ethyl N-(di-2-methylphenoxyphosphonomethyl)glycinate as a yellow oil which gave the following analysis.

Calc'd. C, 60.47; H, 6.41; N, 3.71. Found: C, 60.35; H, 6.64; N, 3.51.

EXAMPLE 6

Di-4-t-butylphenyl phosphite was reacted with N-methylene ethyl glycinate trimer employing benzene as the solvent in accordance with the above procedure to yield ethyl N-(di-4-t-butylphenoxyphosphonomethyl)glycinate as a clear viscous liquid which gave the following analysis:

Calc'd. C, 65.06; H, 7.86; N, 3.03. Found: C, 65.28; H, 8.24; N, 3.02.

EXAMPLE 7

Di-2-methoxyphenyl phosphite was reacted with N-methylene ethyl glycinate trimer employing benzene as the solvent in accordance with the above procedure to yield ethyl N-(di-2-methoxyphenoxyphosphonomethyl)glycinate as a yellow oil which gave the following analysis:

Calc'd. C, 55.75; H, 5.91; N, 3.42. Found: C, 55.60; H, 5.99; N, 3.54.

EXAMPLE 8

The ethyl N(di-4-nitrobenzyloxy phosphonomethyl)glycinate prepared in Example 2 was allowed to stand at room temperature and exposed to the atmosphere for approximately 7 days, during which time a white solid formed. This white solid was identified as ethyl N-[hydroxy(4-nitrobenzyloxy)phosphonomethyl]glycinate which had a melting point of 202°–206° C. and gave the following analysis.

Calc'd. C, 43.38; H, 5.16; N, 8.43. Found: C, 43.58; H, 5.00; N, 8.30.

EXAMPLE 9

Ethyl N(diphenoxyphosphonomethyl)glycinate was dissolved in acetone and sufficient water added to form a cloudy mixture. The mixture was refluxed for four hours and then reduced to dryness. The residue was extracted with a chloroform-water mixture, the aqueous layer vacuum evaporated to dryness and then recrystallized from a chloroform-acetone mixture to yield a white solid having a melting point of 187°–199° with decomposition. The white solid was identified as ethyl N[hydroxy (phenoxy)phosphonomethyl]glycinate and gave the following analysis.

Calc'd. C, 48.36; H, 5.90; N, 5.13. Found: C, 47.93; H, 5.86; N, 5.16.

EXAMPLE 10

The ethyl(di-4-chlorobenzyloxy-phosphonomethyl)glycinate prepared in Example 4 was dissolved in acetone containing 1 to 3% water by volume as the solvent and stirred for 24 hours exposed to the atmosphere. The solvent was removed by vacuum evaporation and the residue dissolved in chloroform. Iscoctane was added to yield a solid precipitate which was removed by filtration. The filtrate was evaporated to yield an oil which upon standing about 3 days and stirring in toluene yielded a white solid which was collected by vacuum filtration. The white solid identified as ethyl N-[hydroxy-(4-chlorobenzyloxy)phosphonomethyl]glycinate had a melting point of 185°–190° with decomposition and gave the following percentage analysis.

Calc'd. C, 44.80; H, 5.33; N, 4.35. Found: C, 44.78; H, 5.42; N, 4.19.

EXAMPLE 11

A benzene solution of (5.76 g, 0.0167 mole) N-methylene ethyl glycinate trimer and 0.05 mol (14.50 g) of di(4-methyl benzyl) phosphite was refluxed 17 hours, concentrated, let stand six weeks as an oil. A solid was present. The mixture was stirred in acetone and then filtered to collect a white solid (1.1 g) identified as ethyl N-[hydroxy(4-methylbenzyloxy)phosphonomethyl]glycinate having a m.p. 157.5° to 159.5° C. and which gave the following analysis.

Calc'd. C, 51.83; H, 6.69; N, 4.65. Found: C, 52.00; H, 6.66; N, 4.70.

EXAMPLE 12

A stirred solution of di(3-nitrophenyl)phosphite and N-methylene ethyl glycinate trimer in 30 ml. of benzene was refluxed for 4 hours and allowed to cool to room temperature with stirring. A suspension of a solid was obtained. The mixture was filtered to yield 2.0 grams of a tan solid identified as ethyl N-[hydroxy(3-nitrophenoxy)phosphonomethyl]glycinate having a melting point of 171°–172° C. and had the following analysis.

Calc'd. C, 41.52; H, 4.75; N, 8.80. Found: C, 41.54; H, 4.57; N, 8.62.

EXAMPLE 13

A suspension of 5.5 g ethyl N-di-(4-methoxyphenoxyphosphonomethyl)glycinate in a water-acetone solvent mixture (10 parts H$_2$O to 15 parts acetone by volume) was stirred for 21 hours until a clear faint yellow solution was formed. This solution was added to 30 ml. of water and extracted with methylene chloride. The aqueous solution was concentrated under vacuum to yield a solid identified as ethyl N[hydroxy(4-methoxyphenoxy)phosphonomethyl]glycinate hemihydrate. The methylene chloride extract was evaporated to dryness and then dissolved in 5 ml. of acetone and 30 ml. water and refluxed (70°–75° C.) for approximately 17 hours. The mixture was extracted with methylene chloride and the water solution evaporated to dryness under vacuum yielding 1.6 g of a white solid identified as the hemihydrate and having a melting point of 162°–164° C. and had the following analysis.

Calc'd. C, 46.16; H, 6.13; N, 4.49. Found: C, 46.11; H, 5.83; N, 4.66.

EXAMPLE 14

Following the above procedure but employing di(4-chlorophenyl) phosphite, ethyl N-[hydroxy(4-chlorophenoxy)phosphonomethyl]glycinate was obtained as a white solid, m.p. 205°–207° C. in 11% yield. The compound gave the following analysis.

Calc'd. C, 42.94; H, 4.91; N, 4.55. Found: C, 42.94; H, 4.70; N, 4.31.

EXAMPLE 15

Di(biphenylyl) phosphite (6.73 g) and N-methylene ethyl glycinate trimer (2.3 g, 0.00667 mole) was dissolved in 50 ml. of benzene and heated to reflux for 2½ hours. An additional 1 g. of the phosphite was added (total 0.02 mole) and refluxed for an additional 30 minutes. The solution was filtered through diatomaceous earth and concentrated to give 3.2 g of an oil. The oil was diluted with 25 ml. acetone and 10 ml. of water added and heated to reflux overnight. A suspension was formed. The suspension was filtered, washed with acetone and dried to a white solid, identified as ethyl N-[hydroxy(4-phenyl-phenoxy) phosphonomethyl]glycinate having a melting point of 209°–210° C. and which gave the following analysis.

Calc'd. C, 58.45; H, 5.77; N, 4.01. Found: C, 58.78; H, 5.70; N, 3.87.

EXAMPLE 16

Di(4-carbethoxyphenyl)phosphite (0.02 moles) and N-methylene ethyl glycinate trimer (0.00667 mole) were dissolved in benzene, hydrochloric acid added and the mixture heated to reflux for 2½ hours to yield the hydrochloride salt of ethyl N-[di(4-carbethoxyphenoxy)phosphonomethyl]glycinate. The glycinate hydrochloride salt was dissolved in 45 ml. of warm benzene and 1 ml. of triethyl amine added. The resulting suspension was filtered after standing 20 minutes at room temperature and the filtrate concentrated under vacuum to yield a yellow oil containing some solid. To the yellow oil was added 25 ml. of benzene and 3 drops of H₂O and the mixture allowed to stand at room temperature (about 25° C.) for 6 days. A white solid formed. The solid was recovered by filtration and washed in hot acetone and dried. The white solid, identified as ethyl N-[hydroxy-(4-carbethoxyphenoxy)phosphonomethyl]glycinate had a melting point of 190°–192° C. and gave the following analysis.

Calc'd. C, 48.70; H, 5.84; N, 4.06. Found: C, 48.35; H, 5.59; N, 3.98.

EXAMPLE 17

A stirred solution of di(4-methylthiophenyl)phosphite (0.04 mole) and ethyl N-methylene glycinate trimer (0.0133 mole) in 100 ml. of benzene was refluxed for 3 hours, and then cooled to room temperature. Hydrogen chloride gas was bubbled through the solution for 30 minutes. Diethyl ether (400 ml.) was added and a dark amber oil precipitated. The oil was azeotroped in benzene for two hours, and petroleum ether added to precipitate an oil, which was decanted and concentrated to an amber glass. Benzene (50 ml.) and triethyl amine (5 ml) were added to the glass and after standing 15 minutes the solution was filtered. The filtrate was concentrated to an oil. To the oil was added acetone (37 ml) and water (3 ml) and the mixture refluxed overnight with stirring. A suspension was formed which was cooled to room temperature and filtered to yield a white solid. The solid washed with acetone and dried to give 1.8 gm of a white crystalline solid having a melting point of 201°–202° C. which was identified as ethyl N[hydroxy(4-methylthiophenoxy)phosphonomethyl]-glycinate hemihydrate and gave the following analysis.

Calc'd. C, 45.14; H, 5.68; N, 4.13. Found: C, 44.73; H, 5.45; N, 4.19.

EXAMPLE 18

Employing the procedure of Example 16 with di(3-methyl-4-chlorophenyl)phosphite the hydrochloride salt of ethyl N-[di(3-methyl-4-chlorophenoxy)phosphonomethyl]glycinate was prepared. To a solution of 2.8 g of the hydrochloride salt in 40 ml. of benzene was added triethylamine (1 ml) and the mixture allowed to stand 15 minutes. The mixture was filtered and the filtrate concentrated to a dark oil. To the oil was added acetone (40 ml) and water (2 ml) and the resulting solution refluxed for 18 hours. The solution was cooled to room temperature to yield a white solid. The mixture was filtered and the white solid washed twice with acetone and dried. The white solid was identified as ethyl N-[hydroxy(3-methyl-4-chlorophenoxy)-phosphonomethyl]glycinate hemihydrate having a melting point of 195°–196° C. and the following analysis.

Calc'd. C, 43.58; H, 5.49; N, 4.24. Found: C, 43.46; H, 5.54; N, 4.05.

EXAMPLE 19

Di-(4-t-butylphenyl)phosphite (0.02 mole) and ethyl N-methylene glycinate trimer (0.0067 mol) dissolved in benzene was refluxed for one and one-half hours and then concentrated to an oil. Acetone (30 ml) and water (30 ml) were added to the oil and the resulting emulsion refluxed overnight (16½ hours) yielding a two-layer system. The mixture was allowed to stand for approximately 5.5 days and then filtered to yield a white solid which was washed twice with hot acetone and dried. The solid identified as ethyl N-[hydroxy-(4-t-butylphenoxy)phosphonomethyl]glycinate having a melting point of 178°–179° C. and the following analysis.

Calc'd. C, 54.71; H, 7.35; N, 4.25. Found: C, 54.96; H, 7.07; N, 4.35.

EXAMPLE 20

A stirred solution of 0.02 mole of di(3-trifluoromethylphenyl)phosphite and ethyl N-methylene glycinate trimer (0.0067 mole) in 40 ml. of benzene was refluxed for 2 hours and concentrated under vacuum to yield an oil. The oil was dissolved in acetone (50 ml) and water (3 ml), refluxed for 20 minutes and then cooled overnight. The resultant mixture was filtered to yield 3.2 g of a white solid identified as ethyl N-[hydroxy(3-trifluoromethylphenoxy)phosphonomethyl glycinate] having a melting point of 181°–182.5° C. and the following analysis.

Calc'd. C, 42.24; H, 4.43; N, 4.10. Found: C, 42.23; H, 4.44; N, 4.15.

EXAMPLE 21

To a stirred suspension of 0.02 moles of di(4-nitrophenyl)phosphite in benzene (40 ml) was added 0.02 equivalents of ethyl N-methylene glycinate trimer and refluxed 2 hours. A solid formed. The benzene was decanted while hot and the solid washed 3 times with 50 ml portions of acetone. To the remaining solid was added acetone (150 ml) and the acetone mixture refluxed overnight. The acetone mixture was filtered hot to yield 2.0 g of a white solid identified as ethyl N-[hydroxy(4-nitrophenoxy)phosphonomethyl]glycinate having a melting point of 193°–195° C. and the following analysis.

Calc'd. C, 41.52; H, 4.75; N, 8.80. Found: C, 41.44; H, 4.76; N, 8.80.

EXAMPLE 22

A stirred solution of 0.02 mole of di(3,4-dichlorophenyl)phosphite and 0.00667 mole (0.02 equivalents) of ethyl N-methylene glycinate trimer in 50 ml. of benzene containing 3 drops of water was refluxed for 3½ hours, allowed to cool, 10 ml. of acetone added and allowed to stand overnight at ambient temperature. The suspension obtained was filtered to yield a solid, which was washed with acetone. The solid was boiled in benzene (30 ml) for 45 minutes and 20 ml. of acetone added and filtered. A white solid (1.2g) identified as ethyl N-[hydroxy(3,4-dichlorophenoxy)phosphonomethyl]glycinate having a melting point of 190°–192° C. and the following analysis.

Calc'd. C, 38.62; H, 4.12; N, 4.09. Found: C, 38.72; H, 4.15; N, 4.12.

EXAMPLE 23

A solution of approximately 0.008 mole of 1,2-phenylene phosphite and 0.00267 mole of ethyl N-methylene glycinate trimer in 40 ml of acetone containing 1 ml of water was refluxed overnight. A few crystals were present. The solution was cooled, stoppered and allowed to stand at room temperature for 10 days. The solution was filtered to yield 0.3 g of a white solid identified as ethyl N[hydroxy(2-hydroxyphenoxy)phosphonomethyl]glycinate having a melting point of 193°–194° C. and the following analysis.

Calc'd. C, 45.68; H, 5.58; N, 4.84. Found: C, 45.63; H, 5.58; N, 4.85.

EXAMPLE 24

Following the procedure of Example 12 but employing di(3-chlorophenyl)phosphite, ethyl N-[hydroxy(3-chlorophenoxy)-phosphonomethyl]glycinate was obtained in 70% yield as a white solid having a melting point of 187.5°–189° C. and the following analysis.

Calc'd. C, 42.94; H, 4.91; N, 4.55. Found: C, 42.94; H, 4.94; N, 4.53.

EXAMPLE 25

Following the procedure of Examples 3 and 9 but employing the methyl N-methylene glycinate trimer, one obtains methyl N-[hydroxy(phenoxy)phosphonomethyl]glycinate having a melting point of 201° to 203° C. with decomposition and the following analysis.

Calc'd. C, 46.34; H, 5.44; P, 11.95. Found: C, 46.23; H, 5.41; P, 11.79.

EXAMPLE 26

Following the procedure of Example 20 but employing methyl N-methylene glycinate trimer, one obtains methyl N-[hydroxy(3-trifluoromethylphenoxy)phosphonomethyl]glycinate having a melting point of 188°–190° C. and the following analysis.

Calc'd. N, 4.28; P, 9.47. Found: N, 4.36; P, 9.63.

EXAMPLE 27

Di-(4-bromobenzyl)phosphite (0.020 mol, 8.4 g) and 0.0067 mol (1 equiv. 2.30 g) of N-methylene ethyl glycinate trimer were mixed in benzene, refluxed 16 hours, stirred in acetone exposed to air, and a white solid formed which was collected, mp 193° with decomposition. The solid was identified as ethyl N-[hydroxy(4-bromobenzyloxy)phosphonomethyl]glycinate hemihydrate and gave the following analysis.

Calc'd. C, 38.42; H, 4.84; N, 3.73. Found: C, 38.92; H, 4.66; N, 3.68.

EXAMPLE 28

To ethyl N-[di-(4-methylphenoxy)phosphonomethyl]glycinate prepared as in Examples 1 to 7 (8.07g) was added 20 ml. of acetone and 30 ml. of water and the resulting emulsion refluxed for 20 hours and then cooled. The mixture was extracted twice with 16 ml. portions of chloroform. The aqueous layer was concentrated to yield 1.1g of a tan solid. The chloroform extracts were evaporated to dryness and then 130 ml. of acetone added with stirring for 10 minutes. The resulting suspension was filtered to yield a white solid. The tan solid was stirred in 30 ml. acetone for 10 minutes and filtered to obtain a white solid. The combined amount of the white solid was 2.5 gm. and was identified as ethyl N[hydroxy(4-methylphenoxy)phosphonomethyl]glycinate having a melting point of 186°–188° C. and gave the following analysis.

Calc'd. C, 50.18; H, 6.32; N, 4.88. Found: C, 50.39; H, 6.40; N, 4.79.

EXAMPLE 29

A stirred solution of 0.03 mole di(2-methylphenyl)phosphite and 0.1 mole ethyl N-methylene glycinate trimer in 50 ml. of benzene was refluxed for 3½ hours and the benzene solution concentrated to an oil. To the oil was added 30 ml. acetone and 25 ml. of water and the mixture heated to reflux overnight. Two layers were formed. The top layer was concentrated, 50 ml. of acetone added, allowed to stand 1½ hours and then filtered to yield 0.5 g of a solid. The aqueous layer was then concentrated to yield 3.0 g of white solid. The two solids were combined, 150 ml. of acetone added and then heated to boiling for 5 minutes and filtered while hot to give 1.9 gm. of white solid. The white solid was dissolved in a hot water (25 ml.)-ethanol (50 ml.) mixture, concentrated and then 15 ml. of ethanol and 15 ml. of acetone added. The ethanol-acetone-product mixture was filtered to give 0.5 gram of a white solid melting at 187.5°–189° C. and identified as ethyl N-[hydroxy(2-methylphenoxy)phosphonomethyl]glycinate having the following analysis.

Calc'd. C, 50.18; H, 6.32; N, 4.88. Found C, 50,35; H, 6.38; N, 4.85.

EXAMPLE 30

A stirred solution of 2.0 × $10^{-2}$ mol of di(3,4-dimethylphenyl)phosphite and 2.0 × $10^{-2}$ mol of N-methylene ethyl glycinate trimer in 40 ml. benzene was refluxed for one hour and was then concentrated to an oil. The oil was dissolved in 40 ml. acetone-1 ml. water and refluxed 18 hours. The solution was then allowed to stand at ambient temperature for three days. The solution was then concentrated to an oil and the oil was dissolved 120 ml. boiling water. The solution was washed with two 50 ml. portions of chloroform. The aqueous layer was then concentrated and to the oil was added 75 ml. acetone. The resulting suspension was filtered to give 0.8 g. of white solid N-[hydroxy(3,4- dimethylphenoxy)phosphonomethyl]glycine: m.p. 199°–200° C.

Calc'd. C, 45.52; H, 5.90; N, 4.83. Found C, 45.93; H, 5.96; N, 4.98.

EXAMPLE 31

A stirred solution of $4.0 \times 10^{-2}$ mol of di($\alpha$-napthyl) phosphite and $4.0 \times 10^{-2}$ mol of N-methylene ethyl glycinate trimer in 70 ml. benzene was refluxed for two hours and then allowed to stand. After standing at ambient temperature 13 days, 20 ml. water was added and solution allowed to stand an additional 20 days. To the solution was added 3.8 g. methane sulfonic acid which upon addition of 350 ml. ethyl ether precipitated an oil. The oil was washed in three 300 ml. portions of ethyl ether and then allowed to stand under 300 ml. ethyl ether for 64 hours. The resulting grey mass was stirred in 200 ml. acetone for 15 minutes and then filtered to give 0.7 g of white solid identified as N-[hydroxy($\alpha$-naphthoxy)phosphonomethyl]glycine having a melting point of 200°–202° C., and having the following analysis.

Calc'd. C, 52.89; H, 4.78; N, 4.74. Found C, 52.68; H, 4.88; N, 4.68.

EXAMPLE 32

A stirred solution of $1.2 \times 10^{-2}$ mol ethyl N-[di(2-methoxyphenoxy)phosphinylmethyl]glycinate and $1.2 \times 10^{-2}$ mol water was refluxed for two days in 35 ml. acetone and then allowed to stand at ambient temperature for eight days. The solution was then concentrated to an oil. The oil was stirred in 250 ml. acetone overnight and the resulting suspension was filtered to give 0.3 g. white solid identified as N-[hydroxy(2-methoxyphenoxy)phosphonomethyl]glycine having a melting point of 183.5°–185° C. (evolution of gas).

EXAMPLE 33

A stirred solution of $2.0 \times 10^{-2}$ mol di(2-chlorophenyl) phosphite and $2.0 \times 10^{-2}$ mol N-methylene ethyl glycinate trimer in 50 ml. benzene was refluxed for 2.5 hours and then concentrated to an oil. The oil was then refluxed in 35 ml. acetone and 10 ml. water for 18 hours. To the solution was added 70 ml. water and 30 ml. chloroform and the resulting bilayer solution was boiled for 15 minutes. The bilayer solution was allowed to stand for 3 months and then separated the layers. The aqueous layer was concentrated to an oil and placed under 300 ml. acetone. After standing 8 days the acetone suspension was filtered to give 0.8 g. white solid identified as N-[hydroxy(2-chlorophenoxy)phosphonomethyl]glycine having a melting point of 178.5°–180° C.

EXAMPLE 34

A stirred solution of di-4-fluorophenyl phosphite (0.03 mole) and ethyl N-methylene glycinate trimer (0.01 mole) was refluxed in benzene (40 ml.) for 30 minutes, then allowed to stand at ambient temperature for 2½ hours. The solution was then concentrated and acetone (45 ml.) and water (1.5 ml.) added and allowed to stand at ambient temperature overnight to yield a suspension. The suspension was filtered to yield a white crystalline solid (3.7 g.) identified as ethyl N-[hydroxy(4-fluorophenoxy)phosphonomethyl]glycinate having a melting point of 201°–203° C.

EXAMPLE 35

A solution of di-(2,4-dichlorophenyl)phosphite (0.02 mol) and ethyl N-methylene glycinate trimer (0.0067 mole) dissolved in benzene (40 ml.) was heated to reflux for 20 minutes during which time a solid formed. The mixture was allowed to stand at ambient temperature overnight and then filtered to give 4.4 grams of a solid identified as ethyl N[hydroxy(2,4-dichlorophenoxy)phosphonomethyl]glycinate having a melting point of 193.5° to 195° C.

EXAMPLE 36

A stirred solution of di(4-benzyloxyphenyl)phosphite (0.03 mole) and ethyl N-methylene glycinate trimer (0.01 mole) dissolved in benzene (50 ml.) was heated to reflux for 1 hour and then concentrated to an oil. The oil was dissolved in acetone (50 ml.) containing about 0.1 ml. water and the solution refluxed for 4 days and then allowed to cool. The suspension obtained was filtered to give an off-white solid identified as impure ethyl N[hydroxy(4-benzyloxyphenoxy)phosphonomethyl]glycinate having a melting point of 192°–195° C. The solid was boiled twice with acetone to give a pure sample of the compound which had a melting point of 197°–198° C.

EXAMPLE 37

The ester from Example 5 was dissolved in a benzene-water mixture (9–10 by volume) and heated to reflux for 90 days. A white crystalline solid was isolated by filtration and had a melting point of 214°–216° C. This material was identified as N-[hydroxy(2-methylphenoxy)phosphonomethyl]glycine.

EXAMPLE 38

A stirred solution of 0.05 mole dibenzylphosphite and 0.0167 mole of ethyl N-methylene glycinate trimer in 100 ml. of benzene was refluxed approximately 18 hours and concentrated under vacuum to an oil. The oil was dissolved in acetone and a trace amount of water was added and the mixture was allowed to stand approximately 60 days. The acetone was concentrated under vacuum to give 7.2 g of an oil, which was dissolved in 50 ml. chloroform and extracted 4 times with 30 ml. of water. The aqueous layer was extracted 4 times with ether, filtered through clay, was concentrated to an oil under vacuum, dissolved in ethanol and acetone was added to the cloud point. A solid precipitated overnight and was collected by filtration. The solid had a melting point of 186°–189° C. with decomposition and was identified as N-[hydroxy(benzyloxy)phosphonomethyl]glycine hemihydrate.

EXAMPLE 39

Di-4-methoxyphenyl phosphite (0.05 mole) and ethyl N-methylene glycinate trimer (0.0167 mole) were dissolved in dry benzene and refluxed for 1 hour. Nuclear magnetic resonance spectral analysis indicated that ethyl N[di(4-methoxyphenoxy)phosphonomethyl]glycine had been formed. The benzene was removed under vacuum and the resulting oil dissolved in diethyl ether. Methane sulfonic acid (4.81 g) was dissolved in ether and added dropwise with stirring overnight. An oil formed and the supernatant liquid was decanted. Diethyl ether was added with stirring and again decanted from the oil. The oil was dissolved in benzene and filtered and upon standing a white solid crystallized from the solution and identified as methane sulfonic acid salt of ethyl N[di(4-methoxyphenoxy)phosphonomethyl]-glycinate having a melting point of 109°-114° C.

EXAMPLE 40

Ethyl N-(diphenoxy)phosphonomethyl glycinate (6.90 g) was dissolved in diethyl ether and anhydrous hydrogen chloride bubbled through the solution for 5 minutes. The solution turned cloudy and an oil precipitated. The supernatant liquid was decanted and the oil dissolved in methylene chloride and isooctane added to precipitate the oil. The supernatant liquid was decanted and the excess isooctane removed under vacuum. The oil dissolved in methylene chloride was filtered through clay and the filtrate stripped of methylene chloride on a rotary evaporator under vacuum to yield a yellow oil identified as the hydrochloride salt of ethyl N(diphenoxy)phosphonomethyl glycinate having the following analysis.

Calc'd. C, 52.93; H, 5.49; N, 3.63. Found C, 52.76; H, 5.44; N, 3.82.

EXAMPLE 41

Following the general procedure of Example 39 but employing the proper phosphite and then anhydrous hydrogen chloride, the hydrochloride salt of ethyl N-[di(3-methyl-4-chlorophenoxy)phosphonomethyl]-glycinate was prepared. The material was washed with a chloroform-petroleum ether mixture, decanted and then washed with diethyl ether (200 ml.). The washes were combined and allowed to stand overnight to yield a tan solid. The tan solid after boiling in diethyl ether turned a cream color and had a melting point of 92°-93.5° C. The solid was the hydrochloride salt.

EXAMPLE 42

Following the procedure of Example 39, the methane sulfonic acid salt of ethyl N-[di-4-chlorobenzyloxy)-phosphonomethyl]glycinate was prepared as a solid having a melting point of 88°-90° C.

Following the procedure of Examples 1 to 7, the following esters of N-phosphonomethyl glycine can be prepared:

Ethyl N-(di-4-methylphenoxy)phosphonomethyl glycinate
Ethyl N-(di-3-nitrophenoxy)phosphonomethyl glycinate
Ethyl N-(di-4-chlorophenoxy)phosphonomethyl glycinate
Ethyl N-(di-4-phenylphenoxy)phosphonomethyl glycinate
Ethyl N-(di-4-carbethoxybenzyloxy)phosphonomethyl glycinate
Ethyl N-(di-4-methylthiophenoxy)phosphonomethyl glycinate
Ethyl N-(di-4-chloro-3-methylphenoxy)phosphonomethyl glycinate
Ethyl N-(di-trifluoromethylphenoxy)phosphonomethyl glycinate
Ethyl N-(di-4-nitrobenzylphenoxy)phosphonomethyl glycinate
Ethyl N-(di-3,4-dichlorophenoxy)phosphonomethyl glycinate
Ethyl N-(di-3-chlorophenoxy)phosphonomethyl glycinate
Methyl N-(diphenoxy)phosphonomethyl glycinate
Methyl N-(di-3-trifluoromethylphenoxy)phosphonomethyl glycinate
Ethyl N-(di-4-bromobenzyloxy)phosphonomethyl glycine
Ethyl N-(di-3,4-dimethylphenoxy)phosphonomethyl glycinate
Ethyl N-(di-α-naphthyloxy)phosphonomethyl glycinate
Ethyl N-(di-2-chlorophenoxy)phosphonomethyl glycinate
Ethyl N-(di-4-fluorophenoxy)phosphonomethyl glycinate
Ethyl N-(di-2,4-dichlorophenoxy)phosphonomethyl glycinate
Ethyl N-(di-4-benzyloxyphenoxy)phosphonomethyl glycinate These compounds usually are impure due to the presence of from 5 to 25% by weight of the particular phenol employed to prepare the phosphite. They can be converted to the strong acid salts according to examples 39 to 42 or they can be hydrolyzed to the mono ester of Formula IV by the procedure of Examples 30-33 and 37 and 38.

EXAMPLE 43

The post-emergence herbicidal activity of various compounds of this invention is demonstrated as follows. The active ingredients are applied in spray form to 14 or 21 dayold specimens of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in a greenhouse and the effects are observed and recorded after approximately 4 weeks. The data is given in Tables I, II, III and IV.

The post-emergence herbicidal activity index used in Tables I, II, III and IV is as follows:

| Plant Response | Index |
|---|---|
| 0-24% Inhibition | 0 |
| 25-49% Inhibition | 1 |
| 50-74% Inhibition | 2 |
| 75-99% Inhibition | 3 |
| 100% Inhibition | 4 |

TABLE I

| *Compound | Rate Kg/Ha | Canada Thistle | Cocklebur | Velvet Leaf | Morning Glory | Lambsquarters | Smartweed | Nutsedge | Quackgrass | Johnson grass | Bromus Tectorum | Barnyard Grass |
|---|---|---|---|---|---|---|---|---|---|---|---|---|
| 1 | 4.48 | 3 | 4 | 4 | 4 | 4 | 4 | 2 | 3 | 4 | 3 | 4 |
|   | 11.2 | 4 | 4 | 4 | 4 | 4 | 3 | 3 | 4 | 4 | 4 | 4 |
| 2 | 11.2 | 2 | 1 | 1 | 2 | 4 | 2 | 1 | 2 | 0 | 0 | 3 |
| 3 | 4.48 | 3 | 4 | 3 | 4 | 4 | 4 | 3 | 3 | 3 | 4 | 4 |
| 4 | 11.2 | 0 | — | 0 | 2 | 0 | 4 | 0 | 0 | 0 | 0 | 1 |
| 5 | 4.48 | 3 | 3 | 2 | 3 | 4 | 2 | 2 | 3 | 3 | 1 | 3 |
|   | 11.2 | 3 | 3 | 3 | 3 | 4 | 3 | 1 | 3 | 3 | 2 | 4 |
| 7 | 5.6 | 3 | 3 | 3 | 3 | 3 | 3 | 3 | 3 | 3 | 2 | 4 |

TABLE I-continued

| *Compound | Rate Kg/Ha | Canada Thistle | Cockle-bur | Velvet Leaf | Morning Glory | Lambs-quarters | Smart weed | Nuts-edge | Quack-grass | Johnson grass | Bromus Tectorum | Barnyard Grass |
|---|---|---|---|---|---|---|---|---|---|---|---|---|
|  | 11.2 | 4 | 4 | 4 | 4 | 4 | 4 | 4 | 4 | 4 | 2 | 4 |

*Compounds
1 - Ethyl N-(di-4-methoxyphenoxy)phosphonomethyl glycinate
1-1 Ethyl N-(di-4-nitrobenzyloxy)phosphonomethyl glycinate
3 - Ethyl N-(diphenoxy)phosphonomethyl glycinate
4 - Ethyl N-(di-4-chlorobenzyloxy)phosphonomethyl glycinate
5 - Ethyl N-(di-2-methylphenoxy)phosphonomethyl glycinate
6 - Ethyl N-(di-4-t-butylphenoxy)phosphonomethyl glycinate
7 - Ethyl N-(di-2-methoxyphenoxy)phosphonomethyl glycinate

TABLE II

| *Compound | Rate Kg/Ha | Canada Thistle | Cockle-bur | Velvet Leaf | Morning Glory | Lambs-quarters | Smart weed | Nuts-edge | Quack-grass | Johnson grass | Bromus Tectorum | Barnyard Grass |
|---|---|---|---|---|---|---|---|---|---|---|---|---|
| 1 | 11.2 | 3 | 3 | 3 | 2 | 4 | 3 | 3 | 3 | 1 | 3 | 4 |
| 2 | 4.48 | 4 | 4 | 3 | 3 | 4 | 4 | 3 | 3 | 2 | 3 | 4 |
|  | 11.2 | 3 | — | 3 | 3 | 4 | 4 | 3 | 3 | 3 | 3 | 4 |
| 3 | 4.48 | 1 | 2 | 1 | 3 | 3 | — | 1 | 1 | 3 | 0 | 3 |
|  | 11.2 | 3 | 2 | 1 | 2 | 4 | 4 | 2 | 2 | 1 | 0 | 3 |
| 4 | 5.6 | 2 | 3 | 2 | 3 | 3 | 2 | 2 | 2 | 4 | 0 | 3 |
|  | 11.2 | 2 | 3 | 2 | 2 | 2 | 4 | 2 | 3 | 4 | 1 | 4 |
| 5 | 4.48 | 3 | — | 4 | 4 | 4 | 4 | 3 | 4 | 4 | 1 | 4 |
|  | 11.2 | 3 | 4 | 4 | 3 | 4 | 3 | 2 | 3 | 4 | 3 | 4 |
| 6 | 4.48 | 3 | 4 | 4 | 3 | 4 | 4 | 3 | 4 | 3 | 1 | 4 |
|  | 11.2 | 4 | 4 | 4 | 4 | 4 | 4 | 3 | 4 | 3 | 3 | 4 |
| 7 | 5.6 | 3 | 4 | 2 | 2 | 4 | 4 | 2 | 3 | 3 | 2 | 4 |
|  | 11.2 | 4 | 4 | 2 | 3 | 4 | 4 | 2 | 4 | 3 | 3 | 4 |
| 8 | 5.6 | 2 | 2 | 1 | 2 | 2 | 3 | 2 | 1 | 1 | 0 | 3 |
|  | 11.2 | 2 | 2 | 2 | 2 | 2 | 3 | 2 | 1 | 1 | 0 | 3 |
| 9 | 5.6 | 4 | 2 | 3 | 2 | 4 | 4 | 3 | 4 | 4 | 3 | 4 |
|  | 11.2 | 4 | 3 | 2 | 2 | 4 | 4 | 4 | 3 | 4 | 4 | 4 |
| 10 | 5.6 | 4 | 3 | 3 | 2 | 4 | 4 | 3 | 4 | 4 | 3 | 4 |
|  | 11.2 | 4 | 3 | 3 | 3 | 4 | 4 | 3 | 4 | 4 | 3 | 4 |
| 11 | 5.6 | 3 | 2 | 3 | 2 | 4 | 4 | 3 | 4 | — | 3 | 4 |
|  | 11.2 | 4 | 2 | 2 | 3 | 3 | 4 | 3 | 3 | 4 | 1 | 4 |
| 12 | 5.6 | 4 | 4 | 1 | 1 | 3 | 3 | 1 | 2 | 2 | 1 | 3 |
| 12 | 11.2 | 3 | 4 | 1 | 2 | 3 | 4 | 2 | 3 | 3 | 2 | 3 |
| 13 | 5.6 | 4 | 3 | 2 | 1 | 4 | 4 | 3 | 4 | 4 | 1 | 4 |
|  | 11.2 | 4 | 3 | 3 | 3 | 3 | 4 | 3 | 4 | 4 | 3 | 4 |
| 14 | 5.6 | 4 | 4 | 4 | 3 | 4 | 4 | 3 | 4 | 4 | 4 | 4 |
|  | 11.2 | 4 | 3 | 4 | 3 | 4 | 4 | 4 | 4 | 4 | 4 | 4 |
| 15 | 5.6 | 4 | 3 | 1 | 2 | 4 | 4 | 4 | 4 | 4 | 3 | 3 |
|  | 11.2 | 4 | 4 | 4 | 3 | 4 | 4 | 4 | 4 | 4 | 4 | 4 |
| 16 | 5.6 | 4 | 4 | 3 | 4 | 4 | 3 | 4 | 4 | 4 | 3 | 4 |
|  | 11.2 | 4 | 2 | 2 | 2 | 4 | 3 | 4 | 4 | 4 | 4 | 4 |
| 17 | 5.6 | 4 | 3 | 3 | 1 | 2 | 3 | 2 | 3 | 3 | 2 | 3 |
|  | 11.2 | 4 | 3 | 4 | 4 | 2 | 4 | 3 | 3 | 3 | 4 | 3 |
| 18 | 5.6 | 3 | 4 | 3 | 3 | 4 | 4 | 4 | 4 | 4 | 4 | 4 |
|  | 11.2 | 4 | 4 | 4 | 3 | 4 | 4 | 4 | 4 | 4 | 4 | 4 |
| 19 | 5.6 | 4 | 4 | 3 | 3 | 4 | 4 | 3 | 4 | 3 | 3 | 4 |
|  | 11.2 | 4 | 4 | 3 | 2 | 4 | 4 | 3 | 3 | 4 | 4 | 4 |
| 20 | 5.6 | 2 | 2 | 0 | 1 | 0 | 3 | 2 | 2 | 3 | 1 | 4 |
|  | 11.2 | 2 | 2 | 0 | 1 | 4 | 4 | 2 | 3 | 4 | 1 | 4 |
| 21 | 5.6 | 4 | 4 | 4 | 3 | 4 | 4 | 2 | 4 | 4 | 3 | 4 |
|  | 11.2 | 3 | 4 | 4 | 3 | 4 | 4 | 3 | 4 | 4 | 3 | 4 |
| 22 | 5.6 | 3 | 3 | 3 | 3 | 4 | 3 | 2 | 4 | 3 | 1 | 3 |
|  | 11.2 | 4 | 3 | 3 | 4 | 4 | 3 | 3 | 4 | 4 | 3 | 4 |
| 23 | 5.6 | 4 | 2 | 3 | 1 | 4 | 3 | 3 | 4 | 4 | 2 | 4 |
|  | 11.2 | 4 | 2 | 3 | 2 | 4 | 3 | 4 | 4 | 4 | 2 | 4 |
| 24 | 5.6 | 3 | 4 | 3 | 1 | 4 | 4 | 3 | 4 | 4 | 2 | 4 |
|  | 11.2 | 4 | 3 | 3 | 1 | 3 | 4 | 3 | 4 | 4 | 4 | 4 |
| 25 | 5.6 | 1 | 1 | 0 | 1 | 1 | 1 | 1 | 0 | 0 | 0 | 1 |

TABLE II-continued

| *Com- pound | Rate Kg/Ha | Canada Thistle | Cockle- bur | Velvet Leaf | Morning Glory | Lambs- quarters | Smart weed | Nuts- edge | Quack- grass | Johnson grass | Bromus Tectorum | Barnyard Grass |
|---|---|---|---|---|---|---|---|---|---|---|---|---|
| | 11.2 | 1 | 2 | 1 | 1 | 1 | 2 | 2 | 2 | 1 | 1 | 2 |

*Compounds
1 - Ethyl N-[hydroxy(4-nitrpbenzyloxy)phosphonomethyl]glycinate
2 - Ethyl N[hydroxy(phenoxy)phosponomethyl]glycinate
3 - Ethyl N[hydroxy(4-chlorobenzyloxy)phosphonomethyl]glycinate
4 - Ethyl N-[hydroxy(4-methylbenzyloxy)phosphonomethyl]glycinate
5 - Ethyl N-[hydroxy(3-nitrophenoxy)phosponomethyl]glycinate
6 - Ethyl N[hydroxy(4-methoxyphenoxy)phosphonomethyl]glycinate hemihytdrate
7 - Ethyl N[hydroxy(4-chlorophenoxy)phosphonomethyl]glycinate
8 - Ethyl N[hydroxy(4-phenolphenoxy)phosphonomethyl]glycinate
9 - Ethyl N[hydroxy(4-carbethoxybenzyloxy)phosphonomethyl]glycinate
10 - Ethyl N[hydroxy(4-methylthiophenoxy)phospghonomethyl]glycinate hemihydrate
11 - Ethyl N[hydroxy(4-chloro-3-methylphenoxy)phosphonomethyl]glycinate
12 - Ethyl N[hydroxy(4-t-butylphenoxy)phosphonomethyl]gluycinate
13 - EthylN-[hydroxy(3-trifluoromethylphenoxy)phosphonomethyl]glycinate
14 - Ethyl N-[hydroxy(4-nitrophenylphenoxy)phosphonomethyl]glycinate
15 - Ethyl N-[hydroxy(3,4-dichlorophenoxy)phosphonomethyl]glycinate
16 - Ethyl N[hydroxy(2-hydroxyphenoxy)phosphonomethyl]glycinate
17 - Ethyl N-[hydroxy(3-chlorophenxoy)phosphonomethyl]glycinate
18 - Methyl N-[hydroxy(phenoxy)phosphonomethyl]glycinate
19 - MethylN-[hydroxy(3-trifluoromethylphenoxy)phosphonomethyl]glycinate
20 - Ethyl N-[hydroxy(4-bromobenzyloxy)phosphonomethyl]glycinate
21 - Ethyl N[hydroxy(4-methylphenoxy)phosphonomethyl]glycinate
22 - Ethyl N[hydroxy(2-methylphenxoy)phosphonomethyl]glycinate
23 - Ethyl N[hydroxy(4-fluorophenoxy)phosphonomethyl]glycinate
24 - Ethyl N[hydroxy(2,4-dichlorophenoxy)phosphonomethyl)]glycinate
25 - Ethyl N[hydroxy(4-benzyloxyphenoxy)phosphonomethyl]glycinate

TABLE III

| *Com- pound | Rate Kg/Ha | Canada Thistle | Cockle- bur | Velvet Leaf | Morning Glory | Lambs- quarters | Smart- weed | Nuts- edge | Quack- grass | Johnson grass | Bromus Tectorum | Barnyard Grass |
|---|---|---|---|---|---|---|---|---|---|---|---|---|
| 1 | 5.6 | 3 | 3 | 2 | 2 | 2 | 2 | 3 | 3 | 4 | 1 | 3 |
|  | 11.2 | 2 | 3 | 3 | 2 | 4 | 4 | 3 | 3 | 3 | 2 | 3 |
| 2 | 5.6 | 4 | 4 | 4 | 1 | 4 | 4 | 3 | 4 | 4 | 4 | 4 |
|  | 11.2 | 4 | 4 | 4 | 2 | 4 | 4 | 4 | 4 | 4 | 4 | 4 |
| 3 | 5.6 | 4 | 4 | 4 | 3 | 4 | 4 | 2 | 4 | 4 | 4 | 4 |
|  | 11.2 | 4 | 4 | 4 | 4 | 4 | 4 | 2 | 4 | 4 | 4 | 4 |
| 4 | 5.6 | 4 | 4 | 4 | 4 | 4 | 4 | 4 | 4 | 4 | 4 | 4 |
|  | 11.2 | 4 | 4 | 4 | 4 | 4 | 4 | 4 | 4 | 4 | 4 | 4 |
| 5 | 5.6 | 3 | 3 | 4 | 2 | 3 | 3 | 3 | 3 | 3 | 4 | 4 |
|  | 11.2 | 4 | 4 | 3 | 3 | 4 | 4 | 3 | 4 | 4 | 4 | 4 |
| 6 | 5.6 | 2 | 3 | 1 | 2 | 2 | 2 | 2 | 1 | 3 | 1 | 2 |
|  | 11.2 | 3 | 3 | 1 | 2 | 4 | 4 | 2 | 3 | 3 | 0 | 3 |
| 7 | 5.6 | 1 | 1 | 0 | 2 | 2 | 0 | 2 | 1 | 3 | 1 | 2 |
|  | 11.2 | 1 | 2 | 0 | 2 | 2 | 2 | 2 | 1 | 1 | 1 | 3 |

*Compound
1 - N[hydroxy(α-naphthyloxy)-phosphonomethyl]glycine
2 - N[hydroxy(2-methoxyphenoxy)phosphonomethyl]glycine
3 - N[hydroxy(2-chlorophenoxy)phosphonomethyl]glycine
4 - N[hydroxy(phenoxy)phosphonomethyl]glycine hemihydrate
5 - N[hydroxy(3,4-dimethylphenoxy)phosphonomethyl]glycine hydrate
6 - N[hydroxy(2-methylphenoxy)phosphonomethyl]glycine
7 - N[hydroxy(benzyloxy)phosphonomethyl]glycine hemihydrate

TABLE IV

| *Com- pound | Rate Kg/Ha | Canada Thistle | Cockle- bur | Velvet Leaf | Morning Glory | Lambs- quarters | Smart weed | Nuts- edge | Quack grass | Johnson grass | Bromus Tectorum | Barnyard Grass |
|---|---|---|---|---|---|---|---|---|---|---|---|---|
| 2 | 5.6 | 2 | 4 | 3 | 2 | 4 | 4 | 2 | 1 | 4 | 3 | 4 |
|  | 11.2 | 2 | 3 | 3 | 2 | 2 | 4 | 2 | 3 | 3 | 2 | 4 |
| 1 | 5.6 | 3 | 3 | 3 | 3 | 4 | 4 | 3 | 3 | 4 | 3 | 4 |
|  | 11.2 | 4 | 3 | 3 | 4 | 4 | 4 | 1 | 4 | 4 | 4 | 4 |
| 3 | 5.6 | 4 | 3 | 3 | 2 | 4 | 3 | 2 | 3 | 2 | 3 | 4 |
|  | 11.2 | 4 | 4 | 3 | 2 | 4 | 4 | 2 | 4 | 4 | 4 | 4 |
| 4 | 5.6 | 1 | 1 | 1 | 1 | 1 | 2 | 0 | 0 | 1 | 0 | 2 |
|  | 11.2 | 1 | 1 | 0 | 1 | 1 | 2 | 0 | 0 | 0 | 0 | 2 |

*Compound
1 - Ethyl N-(diphenoxyphosphonomethyl)glycine hydrochloride
2 - Ethyl N-[di-(4-chloro-3-methylphenoxy)phosphonomethyl]glycine hydrochloride
3 - Ethyl N-(di-4-methoxyphenoxyphosphonomethyl)glycine methane sulfonate
4 - Ethyl N-(di-4-chlorobenzyloxyphosphonomethyl)glycine methane sulfonate The preparation of additional representative compounds of the present invention is illustrated in the further examples which follow.

EXAMPLE 44

Di(4-fluorophenyl)phosphite (2.94 g., 0.01 mole) and methyl N-methylene glycinate trimer (1.0 g., 0.0033 mole) were dissolved in benzene (100 ml.) and heated to reflux for 1 hour. The reaction mixture was then concentrated by vacuum evaporation to yield methyl N-[di(4-fluorophenoxy)phosphonomethyl]glycinate as a pale yellow oil, $n_D^{21} = 1.5248$.

EXAMPLE 45

Di(4-methoxyphenyl)phosphite (3.0 g., 0.01 mole) and methyl N-methylene glycinate trimer (1.0 g., 0.0033 mole) were dissolved in benzene (50 ml.) and heated to reflux for 1 hour. The reaction mixture was then concentrated by vacuum evaporation to yield 3.2 g. (81%)

of methyl N-[di(4-methoxyphenoxy)phosphonomethyl]glycinate as a pale yellow oil, $n_D^{21} = 1.5489$. The compound gave the following analysis.

Calc'd. C: 54.71% H: 5.57% N: 3.54%. Found C: 54.86% H: 5.55% N: 3.54%.

EXAMPLE 46

Di(3-chlorophenyl)phosphite (4.43 g., 0.013 mole) and methyl N-methylene glycinate trimer (1.3 g., 0.0043 mole) were dissolved in benzene (100 ml.) and heated to reflux for 1 hour. The reaction mixture was then concentrated by vaccum evaporation to yield methyl N-[di(3-chlorophenoxy)phosphonomethyl]glycinate as a viscous pale yellow oil, $n_D^{21} = 1.5574$.

EXAMPLE 47

A stirred solution of di(2,4,6-trimethylphenyl)phosphite (17.8 g., 0.05 mole) and ethyl N-methylene glycinate trimer (5.8 g., 0.0167 mole) in benzene (75 ml.) was heated to reflux for 2 hours. The amber solution was then concentrated to a dark amber oil which was filtered through celite to yield 15.0 g. (70%) of ethyl N-[di(2,4,6-trimethylphenoxy)phosphonomethyl]glycinate, $n_D^{21} = 1.5359$. The compound gave the following analysis.

Calc'd. C: 63.73% H: 7.44% N: 3.23%. Found C: 63.49% H: 7.53% N: 3.15%.

EXAMPLE 48

A stirred solution of di(3-methyl-4-nitrophenyl)phosphite (12.6 g., 0.03 mole) and methyl N-methylene glycinate trimer (3.0 g., 0.01 mole) in benzene (50 ml.) was heated to reflux for 1 hour and then concentrated to an oil. To the oil was added wet acetone (70 ml.), and the resulting solution was heated to reflux for 0.5 hours. The solution was then held at ambient temperature for two days. The resulting suspension was filtered, and the white solid obtained was washed with acetone (50 ml.) to yield 3.2 g. (33%) of methyl N-[hydroxy(3-methyl-4-nitrophenoxy)phosphonomethyl]glycinate, m.p. 191°-193° C. The compound gave the following analysis.

Calc'd. C: 41.52% H: 4.75% N: 8.80%. Found C: 41.37% H: 4.73% N: 8.72%.

EXAMPLE 49

A benzene solution of di(4-methoxyphenyl)phosphite (3.0 g., 0.01 mole) and methyl N-methylene glycinate trimer (1.0 g., 0.0033 mole) was heated to reflux for 2 hours and then concentrated to an oil. The oil was dissolved in wet acetone, refluxed for 18 hours, cooled and allowed to stand overnight. The white solids which form were collected by filtration and washed with acetone to yield 1.2 g. of methyl N-[hydroxy(4-methoxyphenoxy)phosphonomethyl]glycinate, m.p. 194°-196° C. The compound gave the following analysis.

Calc'd. C: 45.68% H: 5.58% N: 4.84%. Found C: 45.64% H: 5.61% N: 4.82%.

EXAMPLE 50

A solution of the product of Example 46 (2.29 g., 0.005 mole) in wet acetone (50 ml.) was allowed to stand at ambient temperature for 4.5 days before filtering. The solid obtained was washed with acetone (30 ml.) to yield 0.85 g. (54%) of methyl N-[hydroxy(3-chlorophenoxy)phosphonomethyl]glycinate as a light colored solid, m.p. 181°-182° C. The compound gave the following analysis.

Calc'd. C: 40.92% H: 4.43% N: 4.77%. Found C: 40.77% H: 4.41% N: 4.68%.

EXAMPLE 51

A solution of the product of Example 44 (2.4 g., 0.0061 mole) in wet acetone (50 ml.) was allowed to stand at ambient temperature for 5.5 days. The resulting suspension was filtered, and the solid was washed with hot acetone to yield 1.0 g. (62%) of methyl N-[hydroxy(4-fluorophenoxy)phosphonomethyl]glycinate as a white solid, m.p. 204°-205° C. The compound gave the following analysis.

Calc'd. C: 43.34% H: 4.69% N: 5.05%. Found C: 43.32% H: 4.72% N: 5.05%.

EXAMPLE 52

A suspension of the product of Example 50 (4.5 g., 0.016 mole)in acetone (50 ml.) and water (300 ml.) was heated to 95° C. in an oil bath and maintained for 80 hours. The resulting amber solution was concentrated to approximately 40 ml., and acetone (300 ml.) was added. The reaction mixture was swirled and allowed to stand for 1 hour. The mixture was then filtered to yield 2.5 g. (59.5%) of N-[hydroxy(3-chlorophenoxy)phosphonomethyl]glycine in the monohydrate form as a cream colored solid, m.p. 178°-180° C. The compound gave the following analysis.

Calc'd. C: 36.32% H: 4.40% N: 4.71%. Found C: 36.26% H: 4.44% N: 4.72%.

EXAMPLE 53

A mixture of diphenylphosphite (2.9 g., 0.01 mole) and methyl N-methylene glycinate trimer (1.0 g., 0.0033 mole) was heated for 10 minutes at 80° C. and cooled to ambient temperature. The resulting oil was dissolved in chloroform (45 ml.), and p-nitrobenzenesulfonic acid (2.0 g., 0.01 mole) was added to form a suspension which was refluxed for 25 minutes and then cooled. Ethyl ether (200 ml.) was added, and the mixture was allowed to stand overnight. It was then filtered to give a cream colored solid which was dissolved in hot chloroform (115 ml.) and concentrated to 50 ml. Ethyl ether (60 ml.) was added, and the solution was allowed to stand for 30 minutes. The resulting suspension was filtered to yield 3.3 g. of the p-nitrobenzenesulfonic acid salt of methyl N-[di(phenoxy)phosphonomethyl]glycinate as cream colored crystals, m.p. 137°-138° C. The compound gave the following analysis.

Calc'd. C: 49.07% H: 4.27% N: 5.20%. Found C: 48.80% H: 4.23% N: 5.25%.

EXAMPLE 54

A benzene solution of the product of Example 1 (3.0 g., 0.0073 mole) was concentrated and dissolved in chloroform (50 ml.). A 10% ethanol-chloroform solution (90 ml.) of p-nitrobenzenesulfonic acid (1.5 g., 0.0073 mole) was added, followed by addition of ether to the cloud point. Solids which form were collected and washed with ether to yield 2.87 g. of the p-nitrobenzenesulfonic acid salt of ethyl N-[di(4-methoxyphenoxy)phosphonomethyl]glycinate as a white solid, m.p. 71°-75° C. The compound gave the following analysis.

Calc'd. C: 49.02% H: 4.77% N: 4.57%. Found C: 49.08% H: 4.78% N: 4.63%.

EXAMPLE 55

A solution of di(o-tolyl)phosphite (24.8 g., 0.075 mole) and methyl N-methylene glycinate trimer (8.63 g., 0.025 mole) in dry benzene (300 ml.) was heated at reflux for 2.5 hours, cooled and filtered. A benzene/ether solution of methane sulfonic acid (7.2 g., 0.075 mole) was added dropwise. The solids which formed were collected by suction filtration to yield 28.7 g. (81%) of the methane sulfonic acid salt of ethyl N-[di(o-tolyloxy)phosphonomethyl]glycinate as a white solid, m.p. 138°–141° C. The compound gave the following analysis.

Calc'd. C: 50.73% H: 5.96% N: 2.96%. Found C: 50.95% H: 5.99% N: 2.90%.

EXAMPLE 56

A benzene solution of the product of Example 1 (3.0 g., 0.0073 mole) was concentrated to an oil and dissolved in chloroform (50 ml.). An acetone (50 ml.) solution of oxalic acid (0.95 g., 0.0073 mole) was added, and a gelatinous precipitate which formed was dissolved in chloroform. Ether was added, and a solid was formed upon evaporation under a stream of nitrogen. The solid was collected by filtration and washed with ether to yield 2.6 g. of the oxalic acid salt of ethyl N-[di(4-methoxyphenoxy)phosphonomethyl]glycinate as a white solid, m.p. 136.5°–138° C. The compound gave the following analysis.

Calc'd. C: 50.51% H: 5.25% N: 2.80%. Found C: 50.49% H: 5.26% N: 2.86%.

EXAMPLE 57

A benzene solution of trichloroacetic acid (1.2 g., 0.0073 mole) was added to a benzene solution of the product of Example 1 (3.0 g., 0.0073 mole), and the resultant solution was stirred at room temperature for 2 days. The solvent was removed in vacuo to yield 4.1 g. (97%) of the trichloroacetic acid salt of ethyl N-[di(4-methoxyphenoxy)phosphonomethyl]glycinate as a light yellow oil, $n_D^{25} = 1.5417$.

EXAMPLE 58

A chloroform solution of p-toluene sulfonic acid (1.4 g., 0.0073 mole) was added to a chloroform solution of the product of Example 1 (3.0 g., 0.0073 mole) at room temperature, and the resulting solution was stirred for 15 minutes. Diethyl ether (25 ml.) and benzene (25 ml.) were added, and after 45 minutes, isooctane was added to just below the cloud point. There was obtained 4.2 g. (98.6%) of the p-toluene sulfonic acid salt of ethyl N-[di(4-methoxyphenoxy)phosphonomethyl]glycinate in the monohydrate form as a viscous light brown oil, $n_D^{25} = 1.5533$. The compound gave the following analysis.

Calc'd. C: 52.08% H: 5.72%. Found C: 51.97% H: 5.52%.

EXAMPLE 59

A stirred solution of di(2-methoxyphenyl)phosphite (3.2 g., 0.01 mole) and ethyl N-methylene glycinate trimer (1.15 g., 0.0033 mole) in benzene (60 ml.) was refluxed for 1.5 hours and then concentrated to an oil. Half of the reaction mixture was dissolved in chloroform (50 ml.). There was added p-nitrobenzenesulfonic acid (1.0 g., 0.005 mole), and the mixture was refluxed for 2 hours. Ethyl ether was added until the solution became cloudy. After standing for 3 days, the suspension was filtered to give a tan solid. This solid was recrystallized from chloroform/methyl ether, boiled in 3:2 carbon tetrachloride/chloroform, and filtered while hot. The hot solution was concentrated to 75 ml. and allowed to stand overnight at ambient temperature. Ethyl ether (300 ml.) was added to the solution and then filtered after standing for 30 minutes. The solid was washed with acetone to yield the p-nitrobenzenesulfonic acid salt of ethyl N-[di-(2-methoxyphenoxy)phosphonomethyl]glycinate as a white solid, m.p. 146°–147.5° C. The compound gave the following analysis.

Calc'd. C: 49.04% H: 4.74% N: 4.57%. Found C: 48.96% H: 4.74% N: 4.64%.

EXAMPLE 60

The compounds prepared in Examples 44–59 were tested for their post-emergence herbicidal activity according to the procedures set forth in Example 43. The data is given in Table V.

TABLE V

| *Compound | Rate Kg/Ha | Canada Thistle | Cocklebur | Velvet Leaf | Morning Glory | Lambsquarters | Smart weed | Nutsedge | Quackgrass | Johnson grass | Bromus Tectorum | Barnyard Grass |
|---|---|---|---|---|---|---|---|---|---|---|---|---|
| 1 | 5.6 | 4 | 4 | 4 | 3 | 4 | 4 | 2 | 4 | 3 | 4 | 4 |
|   | 11.2 | 4 | 4 | 4 | 4 | 4 | 4 | 2 | 3 | 3 | 4 | 4 |
| 2 | 5.6 | 4 | 4 | 4 | 4 | 4 | 4 | 2 | 4 | 3 | 4 | 4 |
|   | 11.2 | 4 | 4 | 4 | 4 | 4 | 4 | 2 | 4 | 3 | 4 | 4 |
| 3 | 5.6 | 2 | 4 | 4 | 4 | 4 | 4 | 1 | 2 | 2 | 3 | 4 |
|   | 11.2 | 4 | 4 | 3 | 4 | 4 | 4 | 1 | 2 | 2 | 2 | 4 |
| 4 | 5.6 | 4 | 4 | 3 | — | 4 | 4 | 2 | 2 | 1 | 3 | 4 |
|   | 11.2 | 4 | 4 | 4 | — | 4 | 4 | 3 | 2 | 1 | 4 | 4 |
| 5 | 5.6 | — | 4 | 4 | 4 | 4 | 4 | 2 | 2 | 3 | 4 | 4 |
|   | 11.2 | 4 | 4 | 4 | 3 | 4 | 4 | 1 | 3 | 4 | 4 | 4 |
| 6 | 5.6 | 2 | 4 | 4 | 3 | 4 | 4 | 1 | 3 | 1 | 4 | 4 |
|   | 11.2 | — | 3 | 3 | 3 | 4 | 4 | 2 | 3 | 3 | 4 | 4 |
| 7 | 5.6 | 4 | 3 | 4 | 3 | 4 | 4 | 1 | 4 | 1 | 3 | 4 |
|   | 11.2 | 4 | 4 | 4 | 4 | 4 | 4 | 2 | 4 | 2 | 3 | 4 |
| 8 | 5.6 | 4 | 4 | 4 | 4 | 4 | 4 | 3 | 4 | 3 | 3 | 4 |
|   | 11.2 | 4 | 4 | 4 | 4 | 4 | 4 | 3 | 4 | 2 | 3 | 4 |
| 9 | 5.6 | 4 | 4 | 4 | 4 | 4 | 4 | 3 | 4 | 1 | 3 | 4 |
|   | 11.2 | 4 | 4 | 4 | 4 | 4 | 4 | 3 | 3 | 1 | 4 | 4 |
| 10 | 5.6 | 4 | 4 | 4 | 3 | 4 | 4 | 2 | 4 | 1 | 3 | 4 |
|    | 11.2 | 4 | 4 | 4 | 4 | 4 | 4 | 3 | 4 | 2 | 4 | 4 |
| 11 | 5.6 | 4 | 4 | 2 | 4 | 4 | 4 | 3 | 4 | 3 | 4 | 4 |
|    | 11.2 | 4 | 4 | 4 | 4 | 4 | 4 | 3 | 3 | 2 | 4 | 4 |
| 12 | 5.6 | 4 | 3 | 3 | 2 | 4 | 4 | 2 | 4 | 3 | 3 | 4 |
|    | 11.2 | 4 | 4 | 4 | 4 | 4 | 4 | 3 | 4 | 4 | 4 | 4 |
| 13 | 5.6 | 4 | 3 | 2 | 2 | 4 | 4 | 3 | 4 | 3 | 2 | 4 |
|    | 11.2 | 3 | 3 | 2 | 2 | 4 | 4 | 2 | 4 | 3 | 3 | 4 |
| 14 | 5.6 | 4 | 4 | 4 | 2 | 4 | 4 | 3 | 3 | 4 | 4 | 4 |
|    | 11.2 | 4 | 4 | 4 | 2 | 4 | 4 | 4 | 4 | 4 | 4 | 4 |
| 15 | 11.2 | 1 | 1 | 1 | 1 | 2 | 1 | 2 | 1 | 2 | 2 | 2 |
| 16 | 5.6 | 4 | 4 | 4 | 3 | 4 | 4 | 2 | 4 | 2 | 3 | 2 |

TABLE V-continued

| *Compound | Rate Kg/Ha | Canada Thistle | Cockle-bur | Velvet Leaf | Morning Glory | Lambs-quarters | Smart weed | Nuts-edge | Quack-grass | Johnson grass | Bromus Tectorum | Barnyard Grass |
|---|---|---|---|---|---|---|---|---|---|---|---|---|
| | 11.2 | 4 | 4 | 4 | 3 | 4 | 4 | 3 | 4 | 2 | 4 | 4 |

*Compounds
1 - Methyl N-[di(3-chlorophenoxy)phosphonomethyl]glycinate
2 - Methyl N-[di(4-fluorophenoxy)phosphonomethyl]glycinate
3 - p-nitrobenzenesulfonic acid salt of ethyl N-[di(4-methoxyphenoxy)phosphonomethyl]glycinate
4 - Methyl N-[hydroxy(4-methoxyphenoxy)phosphonomethyl]glycinate
5 - Methyl N-[di(4-methoxyphenoxy)phosphonomethyl]glycinate
6 - Ethyl N-[di(4-methoxyphenoxy)phosphonomethyl]glycinate, oxalic acid salt
7 - p-toluene sulfonic acid salt of ethyl N-[di(4-methoxyphenoxy)phosphonomethyl]glycinate
8 - Ethyl N-[di-(4-Methoxyphenoxy) phosphonomethyl]glycinate, trichloroacetic acid salt
9 - Methyl Ethyl N-[hydroxy(3-chlorophenoxy)phosphonomethyl]glycinate
10 - p-nitrobenzenesulfonic acid salt of ethyl N-[di(2-methoxyphenoxy)phosphonomethyl]glycinate
11 - p-nitrobenzenesulfonic acid salt of methyl N-[di(phenoxy)phosphonomethyl]glycinate
12 - Ethyl N-[di(o-tolyloxy)phosphonomethyl]glycinate, methane sulfonate
13 - Methyl N-[hydroxy(3-methyl-4-nitrophenoxy)phosphonomethyl]glycinate
14 - N-[hydroxy(3-chlorophenoxy)phosphonomethyl]glycine
15 - Ethyl N-[di(2,4,6-trimethylphenoxy)phosphonomethyl]glycinate
16 - Methyl N-[hydroxy(4-fluorophenoxy)phosphonomethyl]glycinate The phytotoxicant compositions, including concentrates which require dilution prior to application to the plants, of this invention contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent, particularly where the active ingredient is water soluble.

The phytotoxicant compositions of this invention, particularly liquids, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isethionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalene-sulfonate and sodium N-methyl-N(long chain acid) taurates.

Water-dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible compositions of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert extender, all parts being by weight of the total composition. Where required, from about 0.1 to 2.0 parts by weight of the inert extender can be replaced by a corrosion inhibitor or antifoaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform and usually contains from 5 to about 95 parts by weight active ingredient, from about 0.25 to 25 parts by weight dispersant, and from about 4.5 to 94.5 parts by weight of water.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Although compositions of this invention can also contain other additaments, for example fertilizers, phytotoxicants and plant growth regulants, pesticides and the like used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g. fertilizers, other phytotoxicants, etc., and applied in a single application. Chemicals useful in combination with the active ingredients of this invention either simultaneously or sequentially include for example triazines, ureas, carbamates, acetamides, acetanilides, uracils, acetic acids, phenols, thiolcarbamates, triazoles, benzoic acids, nitriles and the like such as:

3-amino-2,5-dichlorobenzoic acid
3-amino-1,2,4-triazole
2-methoxy-4-ethylamino-6-isopropylamino-s-triazine
2-chloro-4-ethylamino-6-isopropylamino-s-triazine
2-chloro-N,N-diallylacetamide
2-chloroallyl diethyldithiocarbamate
N'-(4-chlorophenoxy)phenyl-N,N-dimethylurea
1,1'-dimethyl-4,4'-bipyridinium dichloride
isopropyl m-(3-chlorophenyl)carbamate
2,2-dichloropropionic acid
S-2,3-dichloroallyl N,N-diisopropylthiolcarbamate
2-methoxy-3,6-dichlorobenzoic acid
2,6-dichlorobenzonitrile
N,N-dimethyl-2,2-diphenylacetamide
6,7-dihydrodipyrido(1,2-a:2',1'-c)-pyrazidiinium salt
3-(3,4-dichlorophenyl)-1,1-dimethylurea
4,6-dinitro-o-sec-butylphenol
2-methyl-4,6-dinitrophenol
ethyl N,N-dipropylthiolcarbamate
2,3,6-trichlorophenylacetic acid
5-bromo-3-isopropyl-6-methyluracil
3-(3,4-dichlorophenyl)-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea
N-1-naphthylphthalamic acid
1,1'-dimethyl-4,4'-bipyridinium salt
2-chloro-4,6-bis(isopropylamino)-s-triazine
2-chloro-4,6-bis(ethylamino)-s-triazine
2,4-dichlorophenyl-4-nitrophenyl ether
alpha, alpha, alpha-trifluoro-2,6-dinitro-N,N-dipropyl-p-toluidine
S-propyl dipropylthiolcarbamate
2,4-dichlorophenoxyacetic acid
N-isopropyl-2-chloroacetanilide
2',6'-diethyl-N-methoxymethyl-2-chloroacetanilide
monosodium acid methanearsonate
disodium methanearsonate
N-(1,1-dimethylpropynyl)-3,5-dichlorobenzamide Fertilizers useful in combination with the active ingredients include for example ammonium nitrate, urea, potash, and superphosphate.

When operating in accordance with the present invention, effective amounts of the glycines are applied to above ground portions of plants. The application of liquid and particulate solid herbicidal compositions to above ground portions of plants can be carried out by conventional methods, e.g. power dusters, boom and hand sprayers and spray dusters. The compositions can also be applied from airplanes as a dust or a spray because of their effectiveness at low dosages. The application of herbicidal compositions to aquatic plants is usually carried out by spraying the compositions on the aquatic plants in the area where control of the aquatic plants is desired.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.012 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e. a phytotoxic or herbicidal amount. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:

1. A compound of the formula

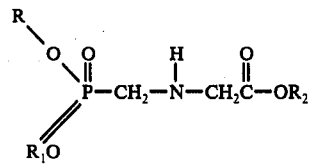

wherein R and $R_1$ are each selected from the group consisting of phenyl, benzyl, naphthyl, biphenylyl, benzyloxyphenyl and phenyl, benzyl or naphthyl groups substituted with from 1 to 3 groups selected from the class consisting of hydroxyl, lower alkyl, lower alkoxy, lower alkylthio, trifluoromethyl, carbo (lower alkoxy), nitro, or halo; and $R_2$ is a lower alkyl group, and the strong acid salts of such compounds.

2. A method which comprises contacting a plant with a herbicidally effective amount of a compound of claim 1.

3. A compound of claim 1 wherein R and $R_1$ are phenyl or said substituted phenyl.

4. A compound of claim 1 wherein R and $R_1$ are benzyl or said substituted benzyl.

5. A compound of claim 1 which is ethyl N-(diphenoxy)phosphonomethyl glycinate.

6. A compound of claim 1 which is ethyl N-(di-4-t-butylphenoxy)phosphonomethyl glycinate.

7. A compound of claim 1 which is ethyl N-(di-2-methylphenoxy)phosphonomethyl glycinate.

8. A compound of claim 1 which is ethyl N-(di-4-nitrophenoxy)phosphonomethyl glycinate.

9. A compound of claim 1 which is ethyl N-(di-4-chlorophenoxy)phosphonomethyl glycinate.

10. A compound of claim 1 which is ethyl N-(dimethoxyphenoxy)phosphonomethyl glycinate.

11. A compound of claim 1 which is a methane sulfonic acid salt.

12. A compound of claim 1 which is an oxalic acid salt.

13. A compound of claim 1 which is a hydrochloric acid salt.

14. A compound of claim 1 which is a p-nitrobenzenesulfonic acid salt.

15. A method which comprises contacting a plant with a herbicidally effective amount of a compound of claim 3.

16. A method which comprises contacting a plant with a herbicidally effective amount of a compound of claim 4.

17. A method which comprises contacting a plant with a herbicidally effective amount of a compound of claim 5.

18. A method which comprises contacting a plant with a herbicidally effective amount of a compound of claim 6.

19. A method which comprises contacting a plant with a herbicidally effective amount of a compound of claim 7.

20. A method which comprises contacting a plant with a herbicidally effective amount of a compound of claim 8.

21. A method which comprises contacting a plant with a herbicidally effective amount of a compound of claim 9.

22. A method which comprises contacting a plant with a herbicidally effective amount of a compound of claim 10.

23. A method which comprises contacting a plant with a herbicidally effective amount of a compound of claim 11.

24. A method which comprises contacting a plant with a herbicidally effective amount of a compound of claim 12.

25. A method which comprises contacting a plant with a herbicidally effective amount of a compound of claim 13.

26. A method which comprises contacting a plant with a herbicidally effective amount of a compound of claim 14.

27. A herbicidal composition which comprises an inert adjuvant and a herbicidally effective amount of a compound of the formula

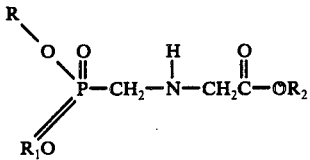

wherein R and $R_1$ are each selected from the group consisting of phenyl, benzyl, naphthyl, biphenylyl, benzyloxyphenyl and phenyl, benzyl or naphthyl groups substituted with from 1 to 3 groups selected from the class consisting of hydroxyl, lower alkyl, lower alkoxy, lower alkylthio, trifluoromethyl, carbo (lower alkoxy), nitro, or halo; and $R_2$ is a lower alkyl group, and the strong acid salts of such compounds.

28. A herbicidal composition of claim 27 wherein R and $R_1$ are phenyl or said substituted phenyl.

29. A herbicidal composition of claim 27 wherein R and $R_1$ are benzyl or said substituted benzyl.

30. A herbicidal composition of claim 27 wherein said compound is ethyl N-(diphenoxy)phosphonomethyl glycinate.

31. A herbicidal composition of claim 27 wherein said compound is ethyl N-(di-4-t-butylphenoxy)phosphonomethyl glycinate.

32. A herbicidal composition of claim 27 wherein said compound is ethyl N-(di-2-methylphenoxy)phosphonomethyl glycinate.

33. A herbicidal composition of claim 27 wherein said compound is ethyl N-(di-4-nitrophenoxy)phosphonomethyl glycinate.

34. A herbicidal composition of claim 27 wherein said compound is ethyl N-(di-4-chlorophenoxy)phosphonomethyl glycinate.

35. A herbicidal composition of claim 27 wherein said compound is ethyl N-(dimethoxyphenoxy)phosphonomethyl glycinate.

36. A herbicidal composition of claim 27 wherein said compound is a methane sulfonic acid salt.

37. A herbicidal composition of claim 27 wherein said compound is an oxalic acid salt.

38. A herbicidal composition of claim 27 wherein said compound is a hydrochloric acid salt.

39. A herbicidal composition of claim 27 wherein said compound is a p-nitrobenzenesulfonic acid salt.

* * * * *

UNITED STATES PATENT AND TRADEMARK OFFICE
CERTIFICATE OF CORRECTION

PATENT NO. : 4,120,689

DATED : October 17, 1978

INVENTOR(S) : Gerard A. Dutra

It is certified that error appears in the above-identified patent and that said Letters Patent are hereby corrected as shown below:

In Table I at the bottom of Columns 13 and 14, the following two lines of data should be inserted immediately after the line of data which begins with "5    4.48". The first of the inserted lines of data has no entry under the heading "Compound".

|   | 11.2 | 2 | 3 | 3 | 4 | 4 | 4 | 3 | 4 | 3 | 2 | 4 |
|---|------|---|---|---|---|---|---|---|---|---|---|---|
| 6 | 4.48 | 3 | 3 | 2 | 2 | 4 | 2 | 2 | 2 | 3 | 1 | 3 |

In Column 17, in the list of Compounds following Table II:

The final word in the name of Compound 6 should be changed from "hemihytdrate" to --hemihydrate--;

In the middle of the name of Compound 8, "phenolphenoxy" should be --phenylphenoxy--.

*Signed and Sealed this*

*Eighteenth* Day of *September 1979*

[SEAL]

Attest:

LUTRELLE F. PARKER

*Attesting Officer*    *Acting Commissioner of Patents and Trademarks*